(12) United States Patent
Bettacchioli

(10) Patent No.: US 9,103,771 B2
(45) Date of Patent: Aug. 11, 2015

(54) DEVICE FOR QUANTIFYING THE DEGASSING OF A PIECE OF EQUIPMENT ARRANGED IN A VACUUM CHAMBER

(75) Inventor: Alain Bettacchioli, Cannes la Bocca (FR)

(73) Assignee: THALES, Courbevoie (FR)

( * ) Notice: Subject to any disclaimer, the term of this patent is extended or adjusted under 35 U.S.C. 154(b) by 365 days.

(21) Appl. No.: 13/634,384

(22) PCT Filed: Feb. 28, 2011

(86) PCT No.: PCT/EP2011/052906
§ 371 (c)(1),
(2), (4) Date: Sep. 12, 2012

(87) PCT Pub. No.: WO2011/110437
PCT Pub. Date: Sep. 15, 2011

(65) Prior Publication Data
US 2013/0000402 A1    Jan. 3, 2013

(30) Foreign Application Priority Data

Mar. 12, 2010    (FR) ...................................... 10 01001

(51) Int. Cl.
*G01N 9/36* (2006.01)
*G01N 29/24* (2006.01)
*G01N 5/04* (2006.01)

(52) U.S. Cl.
CPC .............. *G01N 29/2412* (2013.01); *G01N 5/04* (2013.01); *G01N 9/36* (2013.01); *G01N 2291/0254* (2013.01); *G01N 2291/0256* (2013.01); *G01N 2291/0427* (2013.01)

(58) Field of Classification Search
USPC ................. 73/24.03, 24.04, 24.06, 32 A, 865
See application file for complete search history.

(56) References Cited

U.S. PATENT DOCUMENTS 4,884,446 A * 12/1989 Ljung ......................... 73/504.12
5,684,276 A    11/1997 Altemir
6,041,642 A *  3/2000 Duncan ......................... 73/24.01

FOREIGN PATENT DOCUMENTS

FR           2602589 A1    2/1988

OTHER PUBLICATIONS

Classic Filters, http://194.81.104.27/~brian/DSP/ClassicFilters.pdf, Accessed Oct. 29, 2014.*
English Translation of FR 2602589, Feb. 12, 1988.*

* cited by examiner

*Primary Examiner* — Peter Macchiarolo
*Assistant Examiner* — Alexander Mercado
(74) *Attorney, Agent, or Firm* — Baker & Hostetler LLP

(57) ABSTRACT

A device for quantifying the degassing of a piece of equipment placed in a vacuum chamber includes a metal blade made from a ferromagnetic material including a fixed end and a free end, the blade being provided with a cooling device and a device for measuring an intrinsic temperature of the blade; an electromagnet for exciting the blade; and a measurement sensor for measuring the excitation of the free end of the blade connected to a device for acquiring measurements and for calculating at least one oscillation frequency of the free end of the blade, the acquisition and calculation device being connected to a device for calculating a surface density of a mass deposited on the blade.

8 Claims, 3 Drawing Sheets

DEVICE FOR QUANTIFYING THE DEGASSING OF A PIECE OF EQUIPMENT ARRANGED IN A VACUUM CHAMBER

CROSS-REFERENCE TO RELATED APPLICATIONS

This application is a National Stage of International patent application PCT/EP2011/052906, filed on Feb. 28, 2011, which claims priority to foreign French patent application No. FR 10 01001, filed on Mar. 12, 2010, the disclosures of each of which are incorporated by reference in their entireties.

FIELD OF THE DISCLOSED SUBJECT MATTER

The present invention relates to a device for quantifying the degassing of a piece of equipment placed in a vacuum chamber. It applies notably to the field of equipment tests in a vacuum environment and more particularly to the vacuum degassing tests of space equipment for satellites.

BACKGROUND

During degassing tests of equipment under vacuum, it is desirable to be able to check the end of the passive or active degassing of the equipment in order to decide on the advisability of terminating or extending the duration of the test, or to check that the equipment desorption rate has reached an acceptable level. Checking the end of degassing generally consists in ensuring that the mass of particles degassed by the equipment and collected on a given surface indicated by the dedicated measurement sensor no longer varies over time despite the persistence of the vacuum. The only apparatus known for such measurements is the quartz crystal microbalance, which measures the mass of a deposit on the quartz crystal from the resulting change in the quartz resonance frequency. The measurement taken is very precise, but the data that the quartz crystal microbalance serves to obtain are only satisfactory if the mass of the deposit collected is very low, typically less than about a hundred micrograms per $cm^2$, so that when a clearly identified substance is deposited as a uniformly ordered layer, it is possible to determine the thickness of the deposit therefrom. The determination of the deposit thickness is only important in the context of the semiconductor industry which must take deposit thicknesses into consideration during metallization, oxidation or epitaxy processes, for example. In this case, the deposit thickness never exceeds a few hundred Angströms. On the contrary, during degassing tests under thermal vacuum, this thickness evaluation is less important and it is more advantageous to quantify the mass of pollutant deposited per unit area at various points of the system under test. For equipment undergoing high degassing under thermal vacuum, such as solar panels, for example, this apparatus is saturated too rapidly due to its high sensitivity. It is then necessary to regenerate it very often by evaporating the deposit collected. The operational limitations engendered by these frequent regenerations make the microbalance unsuitable for most thermal vacuum tests, and especially for those dedicated to the degassing of equipment releasing adhesives and solvents, because they can generate deposits with an order of magnitude evaluated in tens of milligrams per $cm^2$.

SUMMARY

It is the object of the invention to remedy the drawbacks of the quartz crystal microbalance and to provide a device for quantifying the degassing of a piece of equipment under vacuum, which measures a surface density of the mass deposited with an accuracy of about a few micrograms per square centimeter, and which is applicable to dense deposits of variable thickness.

For this purpose, according to the invention, the device for quantifying the degassing of a piece of equipment placed in a vacuum chamber comprises a metal blade made from a ferromagnetic material comprising a fixed end and a free end, the blade being provided with a cooling device and a device for measuring the intrinsic temperature of the blade, an electromagnet for exciting the blade, a measurement sensor for measuring the excitation of the free end of the blade connected to a device for acquiring measurements and for calculating at least one oscillation frequency of the free end of the blade, the acquisition and calculation device being connected to a device for calculating the surface density of a mass deposited on the blade.

Advantageously, the electromagnet comprises a periodically powered coil.

Advantageously, the sensor for measuring the excitation of the free end of the blade may consist of a magnet placed opposite the free end of the blade and a coil, the magnet being placed at the center of the coil.

Alternatively, the sensor for measuring the excitation of the free end of the blade may consist of one or two magnets placed directly on the fixed end of the blade and a coil placed opposite the free end of the blade.

Advantageously, the device for acquiring the oscillation frequency of the free end of the blade comprises an analog-to-digital converter and a fourth-order Chebyshev filter.

Advantageously, the quantification device further comprises a device for determining the oscillation frequency of the blade alone in the vacuum chamber for a blade temperature value identical to that corresponding to the blade of which the oscillation frequency is measured.

Advantageously, the device for determining the oscillation frequency of the blade alone comprises a calibration curve of the oscillation frequency of the blade alone as a function of the blade temperature.

The blade temperature can be controlled by means of one or two peltier effect modules.

Advantageously, the oscillation frequency of the blade alone can be corrected as a function of the residual pressure in the caisson when said pressure exceeds $10^{-3}$ hectopascals.

BRIEF DESCRIPTION OF THE DRAWINGS

Other features and advantages of the invention will appear clearly from the rest of the description provided as a purely illustrative and nonlimiting example, with reference to the appended schematic drawings which show.

DETAILED DESCRIPTION

Figure 1:
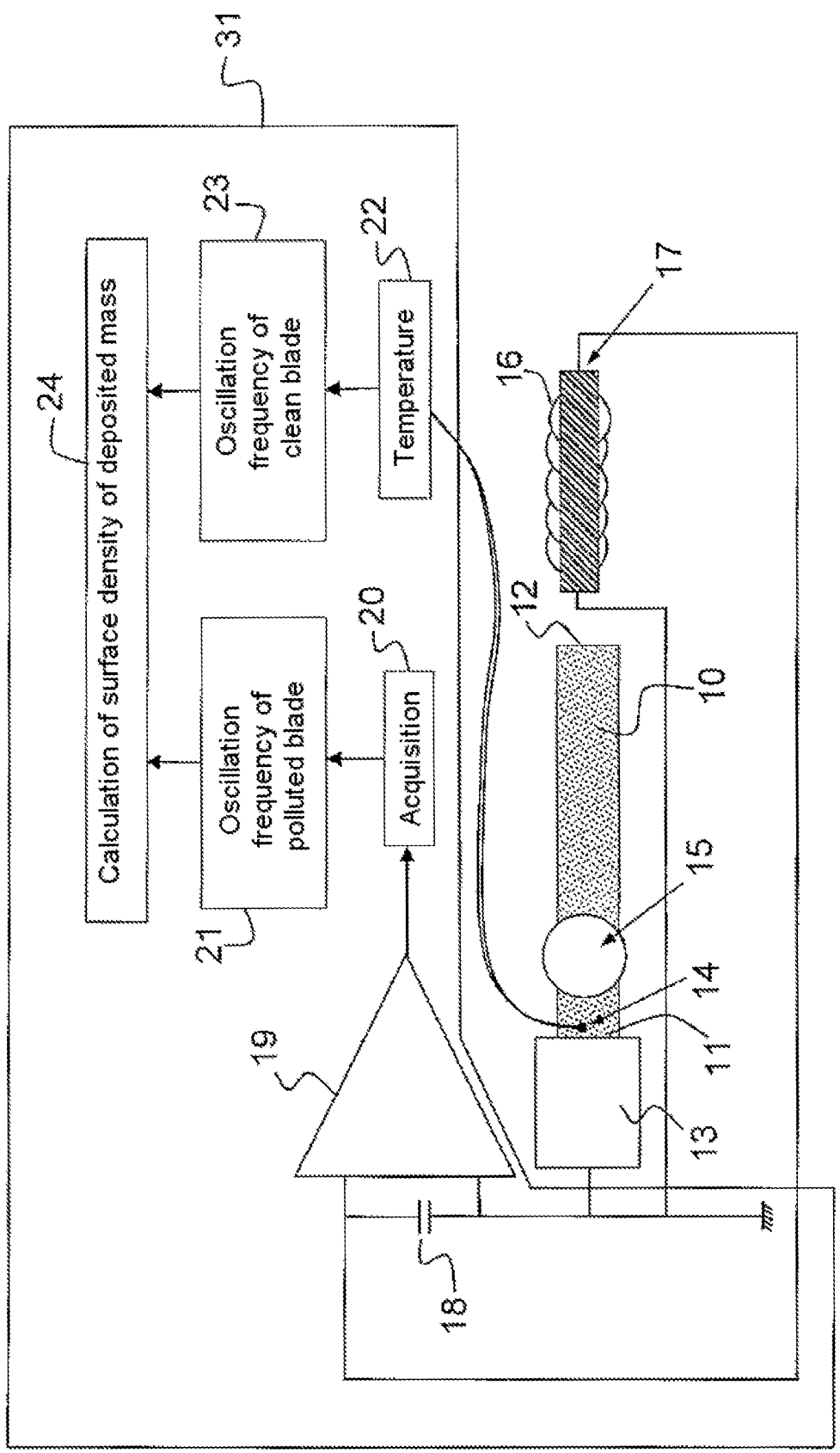
FIG. 1: a schematic side view of an example of a device for quantifying the degassing of a piece of equipment under vacuum, according to the invention.

During the degassing of equipment placed in a vacuum chamber, the main pollutants degassed consist of particles, essentially water and solvents, which condense on the cold surfaces. The proportion of particles dissolved by the equipment decreases as the duration of the vacuum test increases. To quantify the degassing of a piece of equipment under vacuum, the invention therefore consists in measuring the quantity of pollutants deposited on a cold surface consisting of a cooled blade. Due to the solidification temperature of the polluting particles, for example such as water, of which the solidification point is close to 0° C. between atmospheric pressure and 6 hectopascals, to −74° C. approaching $10^{-3}$ hectopascals and about −110° C. approaching $10^{-6}$ hectopascals, the blade temperature must be lower than this lowest temperature value of −110° C.

The device for quantifying the degassing of a piece of equipment under vacuum shown in FIGS. 1 and 3 to 5 is intended to be placed inside a vacuum chamber in the presence of the equipment to be tested. The device comprises a flexible stainless metal blade 10 having ferromagnetic properties, that is to say, a magnetic permeability higher than 0.1, for example, a steel foil containing 0.1% to 2% carbon. For example, the blade 10 may have a thickness of about a tenth of a millimeter, a standard width of 12.7 mm and a length of about 15 cm. The blade 10 comprises a fixed end 11 attached to a fixed support, not shown, and a free end 12. The blade 10 is provided with a cooling device 13 and with a device for measuring its intrinsic temperature, for example a thermocouple. The device 13 for cooling the blade 10 may, for example, comprise a thermal braid connecting the fixed support to a cold source inside the vacuum chamber, or one or two peltier effect modules pressed against the blade, supplied with electricity and thermally connected, for example, by thermal braids 30, to a cold source which serves to remove the heat that they release. An electromagnet 15, which can be placed next to the blade 10, serves to excite the blade 10. The electromagnet 15 comprises a coil powered periodically, the period T being for example equal to one minute, by an electric current pulse having a duration T1 of a few tenths of a second. Under the effect of the electric pulse, the free end 12 of the blade oscillates freely at an oscillation frequency which depends on its mass.

For a blade 10 having a fixed stiffness constant, the higher the mass of the blade, the lower its oscillation frequency. By measuring the oscillation frequency of the clean blade and the oscillation frequency of the blade during the degassing test of the equipment under vacuum, it is therefore possible to determine the mass of pollutant deposited per unit area on the blade 10. Since the oscillation frequency of the blade 10 also depends on its temperature due to the variation in its Young's modulus as a function of temperature, it is necessary to make a preliminary calibration to plot a curve of the variation of the frequency of the clean blade as a function of its temperature. The calibration is made under vacuum for various temperatures of the blade alone, in the absence of any equipment in the vacuum chamber, and the calibration curve obtained is recorded.

Figure 2:
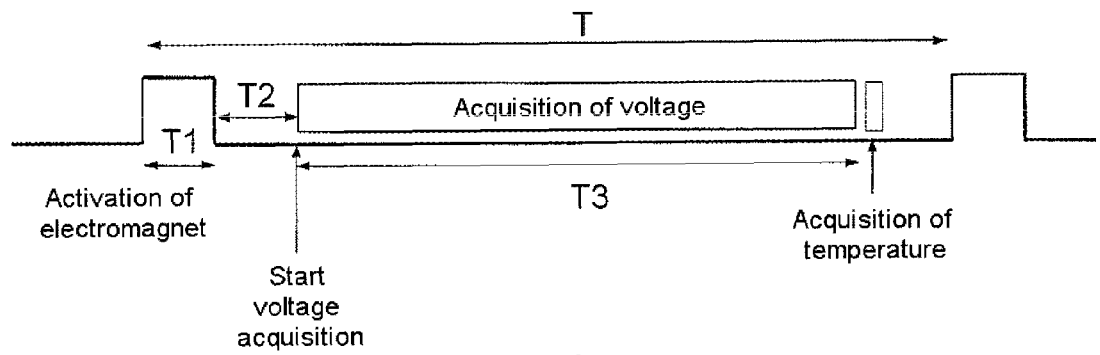
FIG. 2: an example of a chronogram illustrating the acquisition of measurements of the device, according to the invention.
Figure 3:
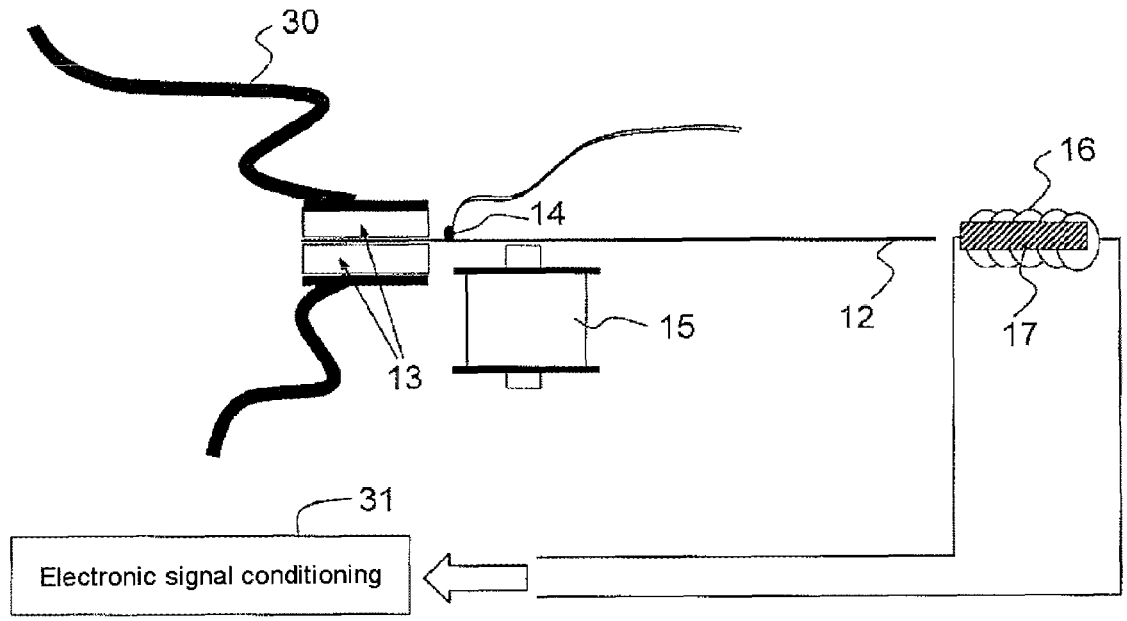
FIG. 3: a schematic plan view of the degassing quantification device in FIG. 1, according to the invention.
Figure 4:
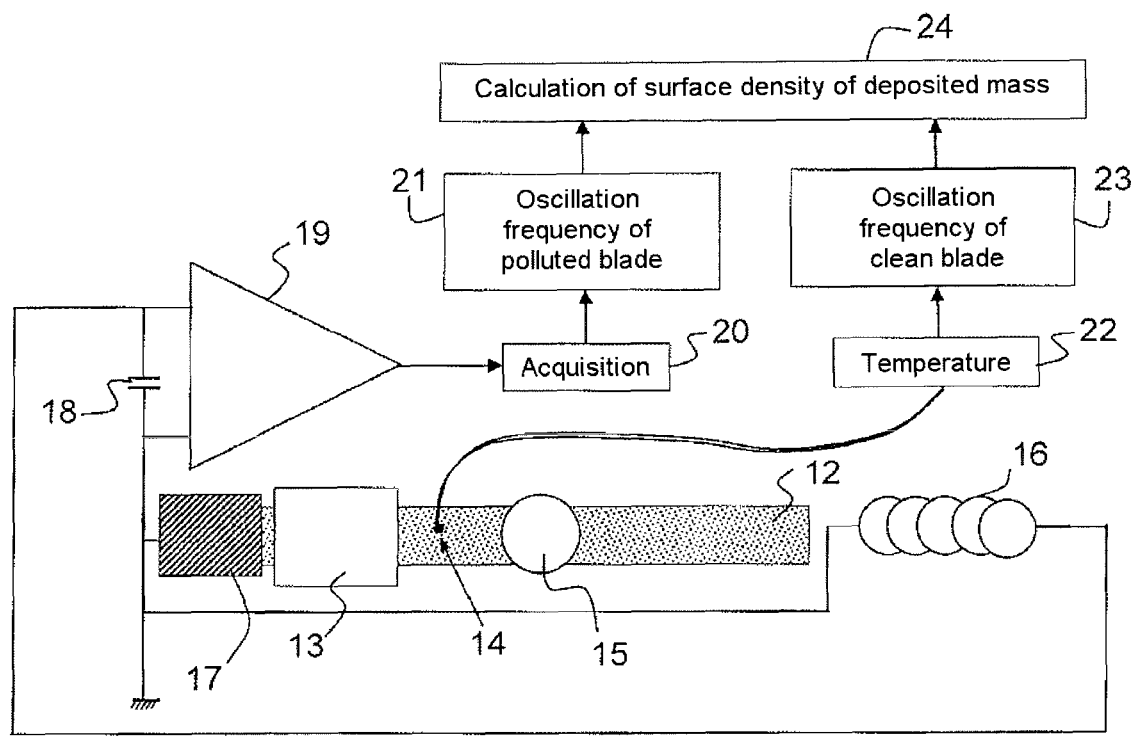
FIG. 4: a schematic side view of an alternative embodiment of the device for quantifying the degassing of a piece of equipment under vacuum, according to the invention.
Figure 5:
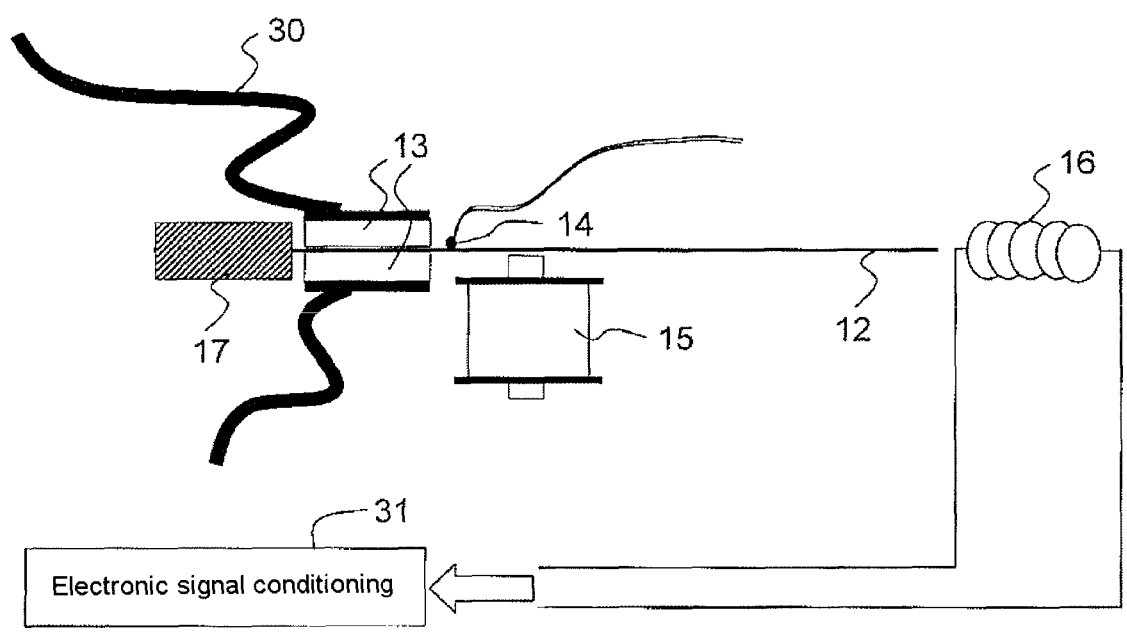
FIG. 5: a schematic plan view of the degassing quantification device of FIG. 4, according to the invention.

The oscillation frequency of the blade 10 is measured using a coil 16 comprising a large number of turns, for example about 10,000 turns. Since the cooled blade 10 is ferromagnetic, its free end is magnetized either by influence with a permanent magnet 17 placed at the center of the coil as shown in FIGS. 1 and 3, or by one or two magnets 13 pressed against the blade 12 as shown in FIGS. 4 and 5. The coil 16, provided or not provided with a central permanent magnet 17, is placed in front of the free end 12 of the blade 10. Since the cooled blade 10 is ferromagnetic, the permanent magnet 17 influences the blade of which the free end is magnetized. When the magnetized blade oscillates, it generates an electromotive force at the terminals of the coil 16 by Lenz effect. The electromotive force at the terminals of the coil 16 has a voltage value which varies as a function of the movement of the magnetized end of the blade and hence as a function of the oscillation frequency of the blade 10. As shown in FIG. 2, the voltage across the terminals of the coil 16 is measured after a latency period T2 following the excitation of the blade, for example T2 may be about one second, thereby serving to overcome a transition period during which the oscillation regime is established and to avoid undesirable effects that would disturb the estimation of the blade oscillation frequency. This precaution is also useful at the low temperatures due to the magnetic remanence which can disturb the beginning of the free oscillations of the blade. On the lapse of the latency period T1, the free oscillation regime of the blade is reached and the acquisition of the voltage delivered by the coil 16 begins with a selected sampling frequency and a predefined duration T3, for example of about 10000 Hz during 15 seconds, which corresponds to 15000 measurement points. The voltage across the terminals of the coil 16 is transmitted to a signal conditioning device 31 in which it is filtered by a capacitor 18 to remove the interfering signals, and then applied to the input of a measurement amplifier 19. The output of the measurement amplifier 19 is connected to a measurement acquisition device 20 comprising an analog-to-digital converter for digitizing the amplified signal and a low-pass filter for selecting a particular oscillation mode and for eliminating the other modes. For example, the mode selected may be the first mode, that is to say, the principal mode. Since the phase of the signal is not used, the filter selected may, for example, be a fourth-order Chebyshev filter comprising cutoff frequencies located at 60% of the central frequency of the filter on either side of this central frequency. After filtration, the digitized signal is transmitted to a device 21 for calculating the oscillation frequency of the polluted blade.

The temperature of the blade 10 can be acquired for example on the expiration of the duration T3 corresponding to the acquisition of the voltage measurements. For this purpose, the thermocouple placed on the blade is connected to a device 22 for acquiring the temperature of the blade. The thermocouple must be electrically isolated from the blade and, for this purpose, it is placed either between two pellets of adhesive kapton having a maximum diameter of 5 mm, or maintained on the blade by a spot of silicon glue. The output of the temperature acquisition device 22 is connected to a device 23 for determining the frequency of the clean blade corresponding to this temperature. The frequency of the clean blade is determined from the calibration curve prepared in the preliminary calibration step.

The oscillation frequencies of the polluted blade and of the clean blade corresponding to the same blade temperature are transmitted to a device 24 for calculating the surface density of the mass deposited on the blade 10.

The surface density σ of the mass deposited on the blade is obtained from the following equation:

$$\sigma = \alpha \left[ \frac{[f^m(T)]^2}{[f_0(T)]^2} - 1 \right]$$

Where σ is the mass deposited per unit area, $f_0$ is the oscillation frequency of the clean blade at temperature T, $f_m$ is the oscillation frequency of the polluted blade at temperature T, and α is a calibration coefficient.

This equation is only valid in a chamber in which the vacuum is at a pressure lower than $10^{-3}$ hectopascals. If the pressure is higher than this value, the oscillation frequency of the blade and the surface density of mass deposited must be corrected to take account of the pressure and composition of the residual gas. This correction enables the apparatus to operate also at the intermediate pressures between $10^{-3}$ hectopascals and atmospheric pressure.

Although the invention has been described in connection with particular embodiments, it is obvious that it is not limited and that it comprises all the technical equivalents of the means described and also their combinations if they fall within the scope of the invention.

The invention claimed is:

1. A quantification device for quantifying the degassing of a piece of equipment placed in a vacuum chamber, the quantification device comprising:
    a metal blade made from a ferromagnetic material comprising a fixed end and a free end, the blade being provided with a cooling device and a measurement device for measuring an intrinsic temperature of the blade;
    an electromagnet for exciting the blade; and
    a measurement sensor for measuring the excitation of the free end of the blade connected to a signal conditioning device comprising an acquisition and calculation device for acquiring measurements and for calculating at least one oscillation frequency of the free end of the blade, the acquisition and calculation device being connected to a calculation device for calculating a surface density of a mass deposited on the blade,
    wherein the cooling device is configured to cool the blade to a temperature lower than a solidification temperature of polluting particles being deqassed in the vacuum chamber.

2. The quantification device as claimed in claim 1, wherein the electromagnet comprises a periodically powered first coil.

3. The quantification device as claimed in claim 2, wherein the sensor for measuring the excitation of the free end of the blade consists of a magnet placed opposite the free end of the blade and a second coil, the magnet being placed at the center of the second coil.

4. The quantification device as claimed in claim 2, wherein the sensor for measuring the excitation of the free end of the blade consists of one or two magnets placed directly on the fixed end of the blade and a coil placed opposite the free end of the blade.

5. The quantification device as claimed in claim 2, wherein the acquisition and calculation device for acquiring the at least one oscillation frequency of the free end of the blade comprises an analog-to-digital converter and a fourth-order Chebyshev filter.

6. The quantification device as claimed in claim 2, wherein the acquisition and calculation device determines an oscillation frequency of a clean form of the blade alone in the vacuum chamber for a temperature value identical to that for which the at least one oscillation frequency is measured for the blade.

7. The quantification device as claimed in claim 2, wherein the acquisition and calculation device for calculating the at least one oscillation frequency of the blade alone comprises a calibration curve of an oscillation frequency of a clean form of the blade alone under vacuum as a function of the blade temperature.

8. The quantification device as claimed in claim 2, wherein the quantification device is configured to correct the oscillation frequency of the blade alone as a function of a residual pressure in the vacuum chamber when said pressure exceeds $10^{-3}$ hectopascals.

* * * * *

UNITED STATES PATENT AND TRADEMARK OFFICE
CERTIFICATE OF CORRECTION

PATENT NO.        : 9,103,771 B2
APPLICATION NO.   : 13/634384
DATED             : August 11, 2015
INVENTOR(S)       : Bettacchioli Page 1 of 1

It is certified that error appears in the above-identified patent and that said Letters Patent is hereby corrected as shown below:

In the claims:

Column 5 line 19 claim 1, replace "deqassed" with --degassed--.

Signed and Sealed this
Twenty-second Day of December, 2015

Michelle K. Lee
*Director of the United States Patent and Trademark Office*